US007638501B1

(12) United States Patent
Naviaux

(10) Patent No.: US 7,638,501 B1
(45) Date of Patent: *Dec. 29, 2009

(54) METHOD OF TREATMENT OF MITOCHONDRIAL DISORDERS

(75) Inventor: Robert K. Naviaux, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/889,251

(22) PCT Filed: Feb. 23, 2000

(86) PCT No.: PCT/US00/04663

§ 371 (c)(1),
(2), (4) Date: Nov. 1, 2001

(87) PCT Pub. No.: WO00/50043

PCT Pub. Date: Aug. 31, 2000

Related U.S. Application Data

(60) Provisional application No. 60/121,588, filed on Feb. 23, 1999.

(51) Int. Cl.
*A61K 31/7072* (2006.01)
(52) U.S. Cl. .......................................... 514/50; 514/45
(58) Field of Classification Search ................ 514/49, 514/50, 45
See application file for complete search history.

(56) References Cited

U.S. PATENT DOCUMENTS

| | | | |
|---|---|---|---|
| 4,960,759 A | 10/1990 | De Luca et al. | 514/50 |
| 5,190,948 A | 3/1993 | Materazzi et al. | 514/274 |
| 5,470,838 A | 11/1995 | von Borstel et al. | 514/50 |
| 5,567,689 A | 10/1996 | Sommadossi et al. | 514/50 |
| 5,583,117 A | 12/1996 | von Borstel et al. | 514/50 |
| 5,691,320 A | 11/1997 | von Borstel et al. | 514/50 |
| 5,723,449 A | 3/1998 | Sommadossi et al. | 514/50 |
| 5,736,531 A | 4/1998 | von Borstel et al. | 514/50 |
| 5,852,000 A | 12/1998 | Ichihara et al. | 514/45 |
| 5,962,459 A | 10/1999 | Piazza et al. | 514/269 |
| 5,968,914 A | 10/1999 | von Borstel et al. | 514/50 |
| 5,981,601 A * | 11/1999 | Nagley et al. | 514/690 |
| 6,020,320 A | 2/2000 | von Borstel et al. | 514/46 |
| 6,020,322 A | 2/2000 | von Borstel et al. | 514/50 |
| 6,054,441 A | 4/2000 | von Borstel et al. | 514/45 |
| 6,232,298 B1 | 5/2001 | von Borstel et al. | 514/49 |
| 6,258,795 B1 | 7/2001 | von Borstel et al. | 514/49 |
| 6,274,563 B1 | 8/2001 | von Borstel et al. | 514/50 |
| 6,297,222 B1 | 10/2001 | von Borstel et al. | 514/45 |
| 6,306,834 B1 | 10/2001 | von Borstel et al. | 514/45 |
| 6,316,426 B1 | 11/2001 | von Borstel et al. | 514/50 |
| 6,329,350 B1 | 12/2001 | von Borstel et al. | 514/50 |
| 6,344,447 B2 | 2/2002 | von Borstel et al. | 514/49 |
| 6,348,451 B1 | 2/2002 | von Borstel et al. | 514/49 |
| 6,472,378 B2 * | 10/2002 | VonBorstel | 514/50 |
| 6,743,782 B1 | 6/2004 | von Borstel et al. | 514/46 |
| 2001/0005719 A1 | 6/2001 | von Borstel | 514/49 |
| 2001/0016576 A1 | 8/2001 | von Borstel | 514/44 |
| 2002/0049182 A1 | 4/2002 | Von Borstel et al. | |

FOREIGN PATENT DOCUMENTS

| | | | |
|---|---|---|---|
| JP | 53056690 | * | 5/1978 |
| WO | WO 89/03837 | | 5/1989 |
| WO | WO 00/11952 | | 3/2000 |
| WO | WO 00/50043 | | 8/2000 |

OTHER PUBLICATIONS website: www.ctnow.com, William Hathaway, The Hartford Courant, Apr. 10, 2001.*
Elverland et al., American Journal of Otology, (Nov. 1991), 12/6, pp. 45-465 (abstract).*
Schorlemmer et al., International Journal of Immunotherapy, (1999) 14(4), pp. 193-204 (abstract).*
The Merck Index, 17$^{th}$ edition (1999), pp. 157-161.*
North et al., Journal of Virology, 1981, p. 987-993.*
Ashour, O.M. et al., "5-(m-Benzyloxybenzyl) Barbituric Acid Acyclonucleoside, A Uridine Phosphorylase Inhibitor, and 2', 3', 5'-tri-O-Acetyluridine, A Prodrug of Uridine, As Modulators of Plasma Uridine Concentration. Implicaitons for Chemotherapy." *Biochem Pharmacol.*, vol. 51, No. 12, Jun. 1996, pp. 1601-1611, (Abstract).
Bjornberg, O. et al., "The Activity of *Escherichia coli* Dihydroorotate Dehydrogenase Is Dependent On a Conserved Loop Identified By Sequence Homolgy, Mutagenesis, and Limited Proteolysis," *Biochemistry*, vol. 38, No. 10, Mar. 9, 1999, (Abstract) pp. 2899-2908.
Bruneau, J.M. et al., "Purification of Human Dihydro-Orotate Dehydrogenase and Its Inhibition by a A77 1726, the Active Metabolite of Leflunomide," *Biochem. J.*, vol. 336, Part 2, Dec. 1, 1998, (Abstract) pp. 299-303.
Chariot, P. et al., "Zidovudine-Induced Mitochondrial Disorder with Massive Liver Steatosis, Myopathy, Lactic Acidosis, and Mitochondrial DNA Depletion," *J. Hepatol.*, vol. 30, No. 1, Jan. 1999, (Abstract) pp. 156-160.
Cheong H.I. et al., "Hereditary Glomerulopathy Associated With A Mitochondrial tRNA (Leu) Gene Mutation," *Pediatr. Nephrol.*, vol. 13, No. 6, Aug. 1999, (Abstract) pp. 477-480.
Connolly, Gerald P., "Abnormal Pyrimidine Metabolism Is the Basis of Some Neurological Diseases," *Trends Pharmacol. Sci.*, vol. 19, No. 7, Jul. 1998, p. 252.
Connolly, Gerald P. et al., "Pyrimidines and CNS Regulation," and "McLeod et al. Reply". *TIPS*, vol. 17, No. 1, Mar. 1996, pp. 106-107.
Connolly and Duley, "Uridine and Its Nucleotides: Biological Actions, Therapeutic potentials," *TIPS*, vol. 20, May 1999, pp. 218-225.

(Continued)

*Primary Examiner*—Brian-Yong S Kwon
(74) *Attorney, Agent, or Firm*—DLA Piper LLP (US)

(57) ABSTRACT

In accordance with the present invention, there are provided methods for the treatment of mitochondrial disorders. Invention methods include the administration of a pyrimidine-based nucleoside such as triacetyluridine, or the like. Also provided are methods of reducing or eliminating symptoms associated with mitochondrial disorders. Mitochondrial disorders particularly appropriate for treatment include those attributable to a deficiency of one or more pyrimidines.

28 Claims, No Drawings

OTHER PUBLICATIONS

Costanzi-Strauss, E. et al., "Restoration of Growth Arrest By a p16INK4, p21WAF1, pRB, and p53 is Dependent on the Integrity of the Endogenous Cell-Cycle Control Pathways in Human Glioblastoma Cell Lines," *Exp. Cell Res.*, vol. 238, No. 1, Jan. 10, 1998, (Abstract) pp. 51-62.

Damore, M.E. et al., "Early Onset of Diabetes Mellitus Associated With the Mitochondrial DNA T14709C Point Mutation: Patient Report and Literature Review," *J. Pediatr. Endocrinol. Metab.*, vol. 12, No. 2, Mar.-Apr. 1999, (Abstract) pp. 207-213.

De la Asuncion, J.G. et al., "AZT Treatment Induces Molecular and Ultrastructural Oxidative Damage to Muscle Mitochondria. Prevention By Antioxidant Vitamins," *J. Clin. Invest.*, vol. 102, No. 1, Jul. 1998, (Abstract) pp. 4-9.

De Muys, J.M. et al., "Anti-Human Immunodeficiency Virus Type 1 Activity, Intracellular Metabolism, and Pharmacokinetic Evaluation of 2'-deoxy -3'-oxa-4'-thiocytidine," *Antimicrob. Agents Chemother.*, vol. 43, No. 8, Aug. 1999, (Abstract) pp. 1835-1844.

Fox, R.I., "Mechanism of Action of Leflunomide in Rheumatoid Arthritis," *J. Rheumatol. Suppl.*, vol. 53, Jul. 1998, (Abstract) pp. 20-26.

Graff, C. et al., "Mitochondrial Medicine—Recent Advances," *J. Intern. Med.*, vol. 246, No. 1, Jul. 1999, (Abstract) pp. 11-23.

Gregoire, Michel et al., "On Auxotrophy for Pyrimidines of Respiration-Deficient Chick Embryo Cells," *Euro. J. Biochem.*, vol. 142, 1984, pp. 49-55.

Janssen, G.M. et al., "The Diabetes-Associated 3243 Mutation In the Mitochondrial tRNA (Leu(UUR)) Gene Causes Severe Mitochondrial Dysfunction Without A Strong Decrease In Protein Synthesis Rate," *J. Biol. Chem.*, vol. 274, No. 42, Oct. 15, 1999, (Abstract) pp. 29744-29748.

Jockel, J. et al., "Structural and Functional Comparison of Agents Interfering with Dihydroorotate, Succinate and NADH Oxidation of Rat Liver Mitochondria," *Biochem. Pharmacol.*, vol. 56, No. 8, Oct. 15, 1998, (Abstract) pp. 1053-1060.

Kelsen, David P. et al., "Phase I Trial of PN401, an Oral Prodrug of Uridine, to Prevent Toxicity From Fluorouracil in Patients with Advanced Cancer," *Journal of Clinical Oncology*, vol. 15, No. 4, Apr. 1997, pp. 1511-1517.

Knecht and Loffler, "Species-Related Inhibition of Human and Rat Dihydroorotate Dehydrogenase By Immunosuppressive Isoxazol and Chinchoninic Acid Deriviative," *Biochem. Pharmacol.*, vol. 56, No. 9, Nov. 1998, (Abstract) pp. 1259-1264.

Kraft, J. et al., "Biological Effects of the Dihydroorotate Dehydrogenase Inhibitor Polyporic Acid, A Toxic Constituent of the Mushroom *Hapalopilus rutilans*, In Rats and Humans," *Arch. Toxicol.*, vol. 72, No. 11, Nov. 1998, (Abstract) pp. 711-721.

Lehto, M. et al., "High Frequency of Mutations In MODY and Mitochondrial Genes In Scandinavian Patients With Familial Early-Onset Diabetes," *Diabetologia*, vol. 42, No. 9, Sep. 1999, (Abstract) pp. 1131-1137.

Loffler, M. et al., "Dihydroorotat-Ubiquinone Oxidoreductase Links Mitochondria In the Biosynthesis of Pyrimidine Nucleotides," *Mol. Cell Biochem.*, vol. 174., 1997, pp. 125-129.

Masanes, F. et al. "Clinical, Histological and Molecular Reversibility of Zidovudine Myopathy;" *J. Neurol. Sci.*, vol. 159, No. 2, Aug. 14, 1998, (Abstract) pp. 226-228.

Masini, A. et al., "Zidovudine-Induced Experimental Myopathy: Dual Mechanism of Mitochondrial Damage," *J. Neurol. Sci.*, vol. 1666, No. 2, Jul. 1, 1999, (Abstract) pp. 131-140.

Matsuura, N. et al., "The prevalence of Mitochondrial Gene Mutations In Childhood Diabetes In Japan," *J. Pediatr. Endocrinol. Metab.*, vol. 12, No. 1, Jan.-Feb. 1999, (Abstract) pp. 27-30.

Morris, A.A., "Mitochondrial Respiratory Chain Disorders and the Liver," *Liver*, vol. 19, No. 5, Oct. 1999, (Abstract) pp. 357-368.

Nakamura S. et al., "Renal Complications In Patients With Diabetes Mellitus Associated With an A to G Mutation of Mitochondrial DNA at the 3243 Position of Leucine tRNA," *Diabetes Res. Clin. Pract.*, vol. 44, No. 3, Jun. 1999, (Abstract) pp. 183-189.

Naviaux, R. K. et al., "Clinical Experience with Uridine and Triacetyluridine (PN401) Therapy of Mitochondrial Disease," *Presented at the "Mitochondrial Dysfunction in Human Pathology" meeting* Melbourne, Australia, Sep. 7, 1998.

Naviaux, R.K. et al., "Sensitive Assay for Mitochondrial DNA Polymerase Gamma," *Clin. Chem.*, vol. 45, No. 10, Oct. 1999, (Abstract) pp. 1725-1733.

Naviaux, R.K. et al., "Correction of Renal Tubular Acidosis (RTA) in Mitochondrial Disease Patients Treated with Triacetyluridine (PN401)," *Abstract Submitted for Presentation, Society for Inherited Metabolic Disorders Annual Meeting*, Mar. 12-15, 1999.

Otabe, S. et al., "Molecular and Historical Evaluation of Pancreata From Patients with a Mitochondrial Gene Mutation Associated with Impaired Insulin Secretion," *Biochem. Biophys. Res. Commun.*, vol. 259, No. 1, May 1999, (Abstract) pp. 149-156.

Page, Theodore et al., "Developmental Disorder Associated With Increased Cellular Nucleotidase Activity," *Proc. Natl. Acad. Sci. USA*, vol. 94, Oct. 1997, pp. 11601-11606.

Pizzorno, G. et al., "Phase I Clinical and Pharmacological Studies of Benzylacyclouridine, A Uridine Phosphorylase Inhibitor," *Clin. Cancer Res.*, vol. 4, No. 5, May 1998, (Abstract) pp. 1165-1175.

Ruckemann, K. et al., "Leflunomide Inhibits Pyrimidine de Novo Synthesis In Mitogen-Simulated T-Lymphocytes from Healthy Humans," *J. Biol. Chem.*, vol. 273, No. 34, Aug. 21, 1998, (Abstract) pp. 21682-21691.

Schwartz et al., "Oral Triacetyluridine (TAU) as A Rescue Agent for 5-Fluotouracil (5FU): Phase I and Pharmacological Study," *Proc. Am. Soc. Clin. Oncol.*, (13, 30 Meet., 134, 1994), Abstract.

Smith P.R. et al., "Pigmentary Retinal Dystrophy and the Syndrome of Maternally Inherited Diabetes and deafness Caused By the Mitochondrial DNA 3243 tRNA (Leu) A to G Mutation," *Ophthalmology*, vol. 106, No. 6, Jun. 1999, (Abstract) pp. 1101-1108.

Szabados, E. et al., "Role of Reactive Oxygen Species and Poly-ADP-Ribose Polymerase In the Development of AZT-Induced Cardiomyopathy In Rat," *Free Radic. Biol. Med.*, vol. 26, No. 3-4, Feb. 1999, (Abstract) pp. 309-317.

van Groeningen, C.J. et al., "Clinical and Pharmacologic Study of Orally Administered Uridine," *Journal of the National Cancer Institute*, vol. 83, No. 6, Mar. 20, 1991, pp. 437-441.

van Groeningen, C.J. et al., "Modulation of Fluorouracil Toxicity with Uridine," *Semin. Oncol.*, vol. 19, 2 Supp. 3, 1992, (Abstract) pp. 148-154.

Yu, Alice L. et al., "Pyrimidine Responsive Syndrome of Neurologic Dysfunction and Susceptibiolity to Infection," *Ped Res*, vol. 41, 1997, Abstract, p. 639.

\* cited by examiner

METHOD OF TREATMENT OF MITOCHONDRIAL DISORDERS

This application is a 371 of PCT/US00/04663 filed Feb. 23, 2000 which claims a benefit of 60/121,588 filed Feb. 23, 1999.

FIELD OF THE INVENTION

The present invention relates generally to mitochondrial disorders, and more specifically to the treatment of mitochondrial disorders by the administration of a pyrimidine-based nucleoside such as triacetyluridine.

BACKGROUND OF THE INVENTION

Mitochondrial diseases occur as inherited, sporadic, and acquired forms. Inherited forms of mitochondrial disease have a high mortality and morbidity. The most severe forms, such as Leigh syndrome (subacute necrotizing encephalomyelopathy) have a mortality of up to 50% per year after diagnosis. Multifactorial forms of mitochondrial disease include much more common disorders such as Huntington's disease, Parkinson's disease, Alzheimer's disease, and even certain forms of diabetes, heart disease, migraine, and stroke. Indeed the process of aging itself has been linked to progressive declines in mitochondrial function.

Mitochondrial diseases are defined as disorders of mitochondrial metabolism that arise from a genetic defect in nuclear or mitochondrial DNA. These may be maternally inherited, inherited as conventional Mendelian disorders, or acquired as new somatic mutations. The disorders may be manifested at any genetic level, from DNA and RNA, to protein. They may affect mitochondrial DNA replication, transcription, the transport of macromolecules into or out of mitochondria, or the function of macromolecules at their site of action within mitochondria. Historically, discussions of pathogenesis in mitochondrial disease have focused on the degradative (oxidative) functions of mitochondria. However, a number of the symptoms of mitochondrial disease may be related to essential biosynthetic (non-degradative) functions of the organelles that are often overlooked. One biosynthetic function of mitochondria is the synthesis of uridine.

Patients with a variety of different mitochondrial disorders may be functionally deficient in uridine because the rate-limiting step in de novo pyrimidine synthesis (Dihydroorotate CoQ Oxidoreductase, EC 1.3.99.11) is located on the inner membrane of mitochondria and coupled to the electron transport chain. Cells with mitochondrial dysfunction in culture are known to be dependent on exogenous uridine for growth and survival because of a functional deficiency in the activity of DHO-QO.

The epidemiology of the inherited forms of mitochondrial disease is largely unknown. It has been estimated that between 1 in 4000 and 1 in 1000 live births in the U.S. will be diagnosed with a mitochondrial disease before the age of 10 years. This is roughly comparable to the incidence of childhood cancer. Degenerative disorders of aging in which mitochondria play a role are, of course, much more common, affecting as many as 20-85 million Americans. Despite the wide-ranging effects of mitochondrial disorders, there is no currently accepted treatment methodology for addressing a problem of such significance and magnitude.

Accordingly, there is still a need in the art for a method for treating mitochondrial disorders, as a class.

BRIEF DESCRIPTION OF THE INVENTION

As a result of the recognition by the inventors of the role of certain pyrimidine-based nucleosides in mitochondrial disorders, the present invention provides a unifying method for the treatment of such. Thus, in accordance with the present invention, there are provided methods for the treatment of a mitochondrial disorder. Invention methods include administering to a subject having or at risk of having such disorder an effective amount of a compound of Formula I:

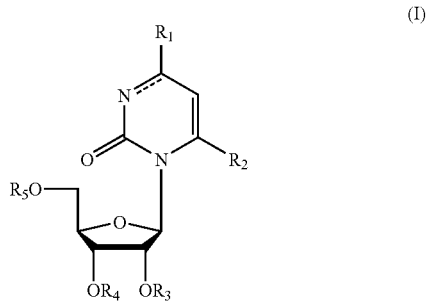

(I)

wherein:

$R_1$ is OH, $NHCOCH_3$, or $NH_2$, $R_2$ is H, $CO_2H$, or

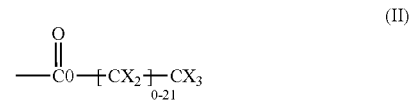

(II)

wherein:

X is $C_1$-$C_{22}$ alkyl, $C_1$-$C_{22}$ alkenyl or $C_1$-$C_{22}$ alkynyl, with substituents selected from the group consisting of H, $C_{1-3}$ alkyl, OH, $NH_2$, and halogen, or wherein X is H, $R_3$, $R_4$, and $R_5$ are, independently, optionally substituted $C_1$-$C_{22}$ alkyl carbonyl, with substituents selected from the group consisting of $C_{1-3}$ alkyl, OH, $NH_2$, halogen, and H, wherein at least one of $R_3$, $R_4$, and $R_5$ is not H.

Exemplary compounds according to Formula (I) include triacetyluridine. Accordingly, in another embodiment of the present invention there are provided methods for the treatment of a mitochondrial disorder. Invention methods include administering to a subject having or at risk of having such disorder an effective amount of 2', 3', 5'-tri-O-acetyl-1-β-D-uridine (hereinafter "triacetyluridine").

In still another embodiment of the present invention there are provided for reducing or eliminating one or more symptoms associated with a mitochondrial disorder. Invention methods include administering to a subject in need thereof an effective amount of a compound of Formula I, wherein $R_1$-$R_5$ and X are as defined above.

Similarly, in another embodiment of the present invention, there are provided methods for reducing or eliminating one or more symptoms associated with a mitochondrial disorder including administering to a subject having or at risk of having such disorder, an effective amount of triacetyluridine.

DETAILED DESCRIPTION OF THE INVENTION

The present invention is based on the discovery that pyrimidine-based nucleosides, such as triacetyluridine and related compounds, effective for treating mitochondrial disorders in which there is a decrease in pyrimidine biosynthesis. The methods of the present invention are an improvement upon the current most commonly used treatments of mitochondrial disorders. This is because pyrimidine-based nucleosides such as triacetyluridine supplement a patient's own production of pyrimidines as well as increasing the systemic levels of pyrimidines. This in turn serves to maintain the natural metabolic and biosynthetic processes of tissues in vivo, especially those tissues with high metabolic load such as in nervous, muscular and organ tissues.

The absence of one or more pyrimidine-based nucleosides has been implicated in a number of disorders which can now be broadly classified as mitochondrial disorders. All of the pyrimidine-based nucleosides (except for orotic acid) can be synthesized using uridine as a starting compound. Thus, a uridine deficiency can result in deficiencies of all other pyrimidine-based nucleosides, and a host of sequalae. As a result, merely supplementing uridine (e.g., by administration of triacetyluridine, or the like) can address a number of symptoms and disease states.

The present invention provides methods for the treatment of mitochondrial disorders by administering one or more of a pyrimidine-based nucleoside, a precursor thereof, or the like.

Organisms contemplated for treatment in accordance with the present invention include any organism with a pyrimidine biosynthetic pathway, including, but not limited to mammals, such as humans, bovine, ovine, equine, feline, canine, and the like.

As used herein, pyrimidine-based nucleosides and precursors thereof include compounds of Formula (I), as follows:

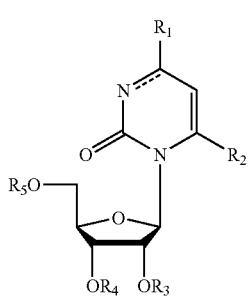

(I)

wherein:

$R_1$ is OH, NHCOCH$_3$, or NH$_2$, $R_2$ is H, CO$_2$H, or

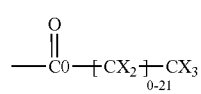

(II)

wherein:

X is $C_1$-$C_{22}$ alkyl, $C_1$-$C_{22}$ alkenyl or $C_1$-$C_{22}$ alkynyl, with substituents selected from the group consisting of H, $C_{1-3}$ alkyl, OH, NH$_2$, and halogen, or wherein X is H, $R_3$, $R_4$, and $R_5$ are, independently, optionally substituted $C_1$-$C_{22}$ alkyl carbonyl, with substituents selected from the group consisting of $C_{1-3}$ alkyl, OH, NH$_2$, halogen, and H, wherein at least one of $R_3$, $R_4$, and $R_5$ is not H.

Alkyl carbonyl R groups contemplated for use in the practice of the present invention include carbonyl derivatives of amino acids (i.e., when the amino substituent is on the α carbon of the alkyl carbonyl), monocarboxylic acids, dicarboxylic acids, and the like. In one aspect of the present invention dicarboxylic acid substituents contemplated for use in the practice of the present invention have in the range of about 3 to 22 carbons.

Carbonyl derivatives of amino acids contemplated for use as substituents in the practice of the present invention include carbonyl derivatives of glycine, L-forms of alanine, valine, leucine, isoleucine, tyrosine, proline, hydroxyproline, serine, threonine, cystine, cysteine, aspartic acid, glutamic acid, arginine, lysine, histidine, carnitine, ornithine, and the like.

Exemplary compounds of Formula I include triacetyluridine, tetracetylcytidine, triacetylorotic acid esters, analogs thereof, and the like. In a presently preferred aspect of the invention, the pyrimidine-based nucleoside is triacetyluridine.

For simplicity, Formula I illustrates the active compounds in the naturally occurring D-configuration, but the present invention also encompasses, isomers (e.g. compounds showing keto-enol tautomersism), compounds in the L-configuration, and mixtures of compounds in the D- and L-configurations, unless otherwise specified. The naturally occurring D-configuration is presently preferred.

The compounds of the invention may be present in the form of their pharmaceutically acceptable salts, such as, but not limited to, an alkali metal salt such as sodium or potassium; an alkaline earth metal salt such as manganese, magnesium, or calcium; or an ammonium or tetraalkyl ammonium salt, i.e., NX'4+ (wherein X is C1-4). Pharmaceutically acceptable salts are salts that retain the desired biological activity of the parent compound and do not impart undesired toxicological effects.

In another embodiment of the present invention, methods for treatment of mitochondrial disorders, and methods for reducing or eliminating symptoms associated with a mitochondrial disorder, further comprise the administration of one or more vitamins and cofactors. Vitamins contemplated for use in accordance with the present invention include thiamine (B1), riboflavin (B2), niacin (B3), pyridoxine (B6), folate, cyanocobalamine (B12), biotin, pantothenic acid, and the like. Co-factors contemplated for use in accordance with the present invention include Coenzyme Q, calcium pyruvate, and the like.

Invention methods are contemplated for use in the treatment of all mitochondrial disorders, particularly those associated with a pyrimidine deficiency, and most particularly those associated with a deficiency in uridine. Specific mitochondrial disorders contemplated for treatment in accordance with the present invention include MELAS (Mitochondrial encephalomyopathy with lactic acidemia and stroke-like episodes), MERRF (Myoclonus, epilepsy, and myopathy with ragged red fibers), NARP/MILS (Neurogenic muscular weakness, ataxia, retinitis pigmentosa/Maternally inherited Leigh syndrome), LHON (Lebers hereditary optic neuropathy) "Mitochondrial blindness", KSS (Kearns-Sayre Syndrome), PMPS (Pearson Marrow-Pancreas Syndrome), CPEO (Chronic progressive external ophthalmoplegia), Leigh syndrome, Alpers syndrome, Multiple mtDNA deletion syndrome, MtDNA depletion syndrome, Complex I deficiency, Complex II (SDH) deficiency, Complex III deficiency, Cytochrome c oxidase (COX, Complex IV) deficiency, Complex V deficiency, Adenine Nucleotide Translocator (ANT) deficiency, Pyruvate dehydrogenase (PDH) deficiency, Ethylmalonic aciduria with lactic acidemia, 3-Methyl glutaconic aciduria with lactic acidemia, Refractory epilepsy with declines during infection, Asperger syndrome with declines during infection, Autism with declines during infection, Attention deficit hyperactivity disorder (ADHD), Cerebral palsy with declines during infection, Dyslexia with declines during infection, materially inherited thrombocytopenia and leukemia syndrome, MNGIE (Mitrochondrial myopathy, peripheral and autonomic neuropathy, gastrointestinal dysfunction, and epilepsy), MARIAHS syndrome (Mitrochondrial ataxia, recurrent infections, aphasia, hypouricemia/hypomyelination, seizures, and dicarboxylic aciduria), ND6 dystonia, Cyclic vomiting syndrome with declines during infection, 3-Hydroxy isobutryic aciduria with lactic acidemia, Diabetes mellitus with lactic acidemia, Uridine responsive neurologic syndrome (URNS), Familial Bilateral Striatal Necrosis (FBSN), Aminoglycoside-associated deafness, Dilated cardiomyopathy, Splenic Lymphoma, Wolfram syndrome, Multiple mitochondrial DNA deletion syndromes, and Renal Tubular Acidosis/Diabetes/Ataxis syndrome.

Another aspect of the present invention is a method of treating a mammal (e.g., human, etc.) with mitochondrial disorders arising from, but not limited to Post-traumatic head injury and cerebral edema, Stroke (invention methods useful for preventing or preventing reperfusion injury), Alzheimer's dementia, Lewy body dementia, Huntington's disease, Amyotrophic lateral sclerosis, Parkinson's disease, Hepatorenal syndrome, Acute liver failure—NASH (non-alcoholic steatohepatitis), Diabetes melitus (particularly TypeII), Anti-metastasis/prodifferentiation therapy of cancer, Idiopathic congestive heart failure, Atrial fibrilation (non-valvular), Wolff-Parkinson-White Syndrome, Idiopathic heart block, Prevention of reperfusion injury in acute myocardial infarctions, Familial migraines, Irritable bowel syndrome, Secondary prevention of non-Q wave myocardial infarctions; Premenstrual syndrome, Prevention of renal failure in hepatorenal syndrome, Anti-phospholipid antibody syndrome, Eclampsia/pre-eclampsia, Oopause infertility, Ischemic heart disease/Angina, and Shy-Drager and unclassified dysautonomia syndromes.

In still another embodiment, there are provided methods for the treatment of mitochondrial disorders associated with pharmacological drug-related side effects. Types of pharmaceutical agents that are associated with mitochondrial disorders include reverse transcriptase inhibitors, protease inhibitors, inhibitors of DHOD, and the like. Specific reverse transcriptase inhibitors include Azidothymidine (AZT), Stavudine (D4T), Zalcitabine (ddC), Didanosine (DDI), Fluoroiodoarauracil (FIAU), and the like. Specific protease inhibitors include RITONAVIR™, INDINAVIR™, SAQUINAVIR™, NELFINAVIR™, and the like. Specific inhibitors of dihydroorotate dehydrogenase (DHOD) include LEFLUNOMIDE™, BREQUINAR™, and the like.

Because certain symptoms of mitochondrial disorders can be associated with one or more pyrimidine-related deficiencies, in another embodiment of the present invention, there are provided methods for reducing or eliminating one or more symptoms associated with a mitochondrial disorder. Symptoms associated with mitochondrial disorders include renal tubular acidosis (RTA), impaired eyesight, dementia, seizures, cardiomyopathy, skeletal myopathy, peripheral myopathy, autonomic myopathy, and the like.

Mitochondrial disorders can be classified according to their effects on certain mitochondria-specific biosynthetic pathways. Thus, in another embodiment of the present invention there are provided methods for the treatment of mitochondrial disorders that are the result of a perturbation or defect in a mitochondrial biosynthetic pathway. A primary biosynthetic pathway of the mitochondria is that for pyrimidine biosynthesis. Because invention methods comprise the administration of pyrimidines, pyrimidine analogs, precursors thereof, biosynthetic pathways contemplated for treatment by invention methods include biosynthetic pathways for pyrimidines, including uridine, thymidine, cytosine, and the like. Specific deficiencies in pyrimidine biosynthetic pathways include those associated with particular enzymes in the pathway of interest. Such deficiencies include, missing enzymes, reduced expression of enzymes, defective (e.g., mutant) enzymes having reduced or no activity, and the like. Specific enzymes include dihydroorotate dehydrogenase (DHOD), uridine monophosphate synthetase (UMPS), and the like.

The present invention further provides pharmaceutical compositions comprising a unit dosage form containing pyrimidine-based nucleosides according to Formula I, analogs thereof, and the like.

The active components described for use herein can be formulated with a pharmaceutically suitable vehicle, selected to render such compositions amenable to delivery by oral, rectal, parenteral (e.g., intravenous, intramuscular, intraarterial, intraperitoneal, and the like), or inhalation routes, osmotic pump, topical, opthalmic, and the like.

Ointments are semi-solid preparations that consist of the active ingredient incorporated into a fatty, waxy, or synthetic base.

Examples of suitable creams include, but are not limited to, water-in-oil and oil-in-water emulsions. Water-in-oil creams may be formulated by using a suitable emulsifying agent with properties similar, but not limited, to those of the fatty alcohols such as cetyl alcohol or cetostearyl alcohol and to emulsifying wax. Oil-in-water creams may be formulated using an emulsifying agent such as cetomacrogol emulsifying wax. Suitable properties include the ability to modify the viscosity of the emulsion and both physical and chemical stability over a wide range of pH. The water soluble or miscible cream base may contain a preservative system and may also be buffered to maintain an acceptable physiological pH.

In addition to the topical method of administration described above, there are various methods of administering the compounds of the present invention systemically. One such means would involve an aerosol suspension of respirable particles comprised of the active compound, which the subject inhales. The active compound would be absorbed into the bloodstream via the lungs and contact the systemic circulation in a pharmaceutically effective amount. The respirable particles may be liquid or solid, with a particle size sufficiently small to pass through the mouth and larynx upon inhalation; in general, particles ranging from about 1 to 10 microns, but more preferably 1-5 microns, in size are considered respirable.

Another means of systemically administering the active compounds to the subject would involve administering a liquid/liquid suspension in the form of nasal drops of a liquid formulation, or a nasal spray of respirable particles which the subject inhales. Liquid pharmaceutical compositions of the active compound for producing a nasal spray or nasal drops may be prepared by combining the active compound with a suitable vehicle, such as sterile pyrogen free water or sterile saline by techniques known to those skilled in the art.

Other means of systemic administration of the active compound would involve oral administration, in which pharmaceutical compositions containing compounds of Formula I, are in the form of a solid, a solution, an emulsion, a dispersion, a micelle, a liposome, and the like, wherein the resulting formulation contains the active compounds contemplated for use herein, in admixture with an organic or inorganic carrier or excipient suitable for nasal, enteral or parenteral applications. The active ingredients may be compounded, for example, with the usual non-toxic, pharmaceutically or physiologically acceptable carriers for tablets, pellets, capsules, troches, lozenges, aqueous or oily suspensions, dispersible powders or granules, suppositories, solutions, emulsions, suspensions, hard or soft capsules, caplets or syrups or elixirs and any other form suitable for use. The carriers that can be used include gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents may be used. The active compounds contemplated for use herein are included in the pharmaceutical formulation in an amount sufficient to produce the desired effect upon administration (i.e., a therapeutically effective amount).

The powder, solution, suspension, or tablet contains the active compound in a physiologically compatible vehicle, as those skilled in the art of oral delivery system development can select using conventional criteria. For example, such formulations may contain one or more agents selected from flavoring agents (such as peppermint, oil of wintergreen or cherry), coloring agents, preserving agents, and the like, in order to provide pharmaceutically elegant and palatable preparations. Tablets containing the active ingredients in admixture with non-toxic pharmaceutically acceptable excipients may also be manufactured by known methods. The excipients used may be, for example, (1) inert diluents, such as calcium carbonate, lactose, calcium phosphate, sodium phosphate, and the like; (2) granulating and disintegrating agents, such as corn starch, potato starch, alginic acid, and the like; (3) binding agents, such as gum tragacanth, corn starch, gelatin, acacia, and the like; and (4) lubricating agents, such as magnesium stearate, stearic acid, talc, and the like. The tablets may be uncoated or they may be coated by known techniques to delay disintegration and absorption in the gastrointestinal tract, thereby providing sustained action over a longer period. For example, a time delay material such as glyceryl monostearate or glyceryl distearate may be employed. The tablets may also be coated by the techniques described in the U.S. Pat. Nos. 4,256,108; 4,160,452; and 4,265,874, incorporated herein by this reference, to form osmotic therapeutic tablets for controlled release.

When formulations for oral use are in the form of hard gelatin capsules, the active ingredients may be mixed with an inert solid diluent, for example, calcium carbonate, calcium phosphate, kaolin, or the like. They may also be in the form of soft gelatin capsules wherein the active ingredients are mixed with water or an oil medium, for example, peanut oil, liquid paraffin, olive oil, and the like.

Additional means of systemic administration of the active compound to the subject would involve a suppository form of the active compound, such that a therapeutically effective amount of the compound reaches the systemic circulation.

The quantity of the active compound (i.e., pyrimidine-based nucleoside of Formula I) included in the pharmaceutical composition is an amount sufficient to ameliorate signs and symptoms of mitochondrial disorders in the subject of from about 0.5 g/m$^2$/day to about 20 g/m$^2$/day, more preferably from about 2 g/m$^2$/day to about 10 g/m$^2$/day, and in an even more preferred embodiment, about 6 g/m$^2$/day. As used herein, the units m$^2$ denote surface area (SA), and are determined by the following formula: SA in m$^2$=(height in cm)$^{0.75}$×(weight in kg)$^{0.425}$×71.84÷10,000.

Depending on the solubility of the particular formulation of active compound administered, the daily dose to ameliorate signs and symptoms of mitochondrial disorders may be divided among one or several unit dose administrations. The total daily dose for triacetyluridine (for example) may range from 1 to 20 grams per day, depending upon the age and state of the subject, given at a regimen of up to five times per day or on an as needed basis to address acute exacerbations.

Co-factors and vitamins to be optionally administered in accordance with invention are to be given at an appropriate daily dosage. Daily dosages contemplated for administration in accordance with invention methods are set out in Table I.

TABLE I

| Coenzyme or vitamin | Range of daily dosages | Presently preferred daily dosage |
| --- | --- | --- |
| Coenzyme Q | about 1-10 mg/kg/day | about 5 mg/kg/day |
| Calcium pyruvate | about 1-6 g/m$^2$/day | about 3 g/m$^2$/day |
| Thiamine (B1) | about 0.5-5 mg/kg/day | about 50-200 mg/day |
| Riboflavin (B2) | about 0.5-5 mg/kg/day | about 50-200 mg/day |
| Niacin | about 0.5-20 mg/kg/day | about 50-200 mg/day |
| Pyridoxine (B6) | about 0.5-5 mg/kg/day | about 50-200 mg/day |
| Folate | about 0.005-0.03 mg/kg/day | about 0.4-2 mg/day |
| Cyanocobalamine (B12) | about 0.001-0.03 mg/kg/day | about 0.05-0.5 mg/day |
| Biotin | about 0.005-0.2 mg/kg/day | about 0.05-0.5 mg/day |
| Pantothenic acid | about 0.5-5 mg/kg/day | about 50-200 mg/day |

As those of skill in the art will understand, the above dosages are general in nature and can be tailored to the individual subject's needs by an appropriate treating health care professional, taking into account the subject's age, weight, size, condition, and the like.

Compounds of Formula I can be made by methods which are well known to those skilled in the art and in accordance with known procedures F. J. M. Rajabalee, Angew. Chem. Int. Ed., vol. 10, p. 75 (1971); some are commercially available, for example, from Sigma Chemical Company, PO Box 14508, St. Louis, Mo. 63178.

The invention will now be described in greater detail by reference to the following non-limiting examples.

Angew. Chem. Int. Ed., vol. 10, p. 75 (1971); some are commercially available, for example, from Sigma Chemical Company, PO Box 14508, St. Louis, Mo. 63178.

The invention will now be described in greater detail by reference to the following non-limiting examples.

EXAMPLES

Example 1

Treatment of Mitochondrial Disease with Triacetyl Uridine

Patients. Four patients with mitochondrial renal tubular acidosis (RTA) were studied. Mitochondrial RTAs often defy simple classification as proximal (type II) or distal (type I) tubulopathies these patients are often mosaics and express features of both phenotypes leading to hyperchloremic (non-anion gap) metabolic acidoses.

Patient #1 was a 2 year old female with Leigh syndrome, lactic acidemia, and complex I deficiency who required 200 mEq/day of NaHCO$_3$ to compensate for renal of alkali, and maintain serum bicarbonate levels above 20 mEq/l, 1+ proteinuria, and significant aminoaciduria with hydroxyprolinuria.

Patient #2 was a 3 year old female with Leigh syndrome, and complex IV (COX) deficiency, who also required 200 mEq/day of $NaHCO_3$.

Patient #3 was a 2 year old male wt Leigh syndrome, lactic acidemia, 1+ proteinuria, and pyruvate dehydrogenase (PDH) deficiency, who required up to 210 mEq/day of $NaHCO_3$.

Patient #4 was an 11 year old male with 3-hydroxyisobutyric aciduria, lactic acidemia, and encephalomyopathy, who required 468 mEq/day of $NaHCO_3$.

Methods. Blood and urine electrolytes, creatinine, pH, urinalysis, and venous blood gases were studied before and after treatment. Quantitative urine amino acids and organic acids were also obtained. Pre-enrollment doses of oral sodium bicarbonate were continued for the first 3 days of triacetyluridine treatment, then reduced weekly as tolerated to maintain serum bicarbonate above 20 mEq/l.

Treatment. Patients received triacetyluridine 2 g/m² PO TID.

Results. Patient #1 experienced complete correction of her RTA within 24 hours of treatment, maintaining a serum bicarbonate of more than 20 mEq/l without any further oral bicarbonate. She also had complete resolution of her hydroxyprolinuria within 2 weeks.

Urinary bicarbonate losses in patient #2 were initially 99 mEq/l. The fractional excretion of bicarbonate ($FE_{HCO3}$) was 9.3% prior to therapy. After 36 hours on treatment with triacetyluridine, urinary bicarbonate losses were undetectable (<5 mEq/l). After 3 weeks of treatment, just 25% of the patient's pre-enrollment dose of bicarbonate was needed to maintain normal serum bicarbonate.

Urinary bicarbonate losses in patient #3 were 59 mEq/l. The $FE_{HCO3}$ was 10.0% prior to therapy. After 36 hours of treatment with triacetyluridine, urinary bicarbonate losses were undetectable (<5 mEq/l). After 3 weeks of treatment the patient required just 10% of his previous dose of bicarbonate.

Following I week of treatment, patient #4 had a 35% reduction in his oral bicarbonate requirement. Treatment is continuing.

Conclusion. Renal tubular acidosis was corrected or dramatically improved in 4 out of 4 patients with mitochondrial disease treated with triacetyluridine.

Example 2

Treatment by Administration of Triacetyluridine to a Subject Having MARIAHS Syndrome Patient. CMZ-child with mitochondrial ataxia, recurrent infections, aphasia, hypouricemia/hypomyelination, and seizures (MARIAHS syndrome), cared for since 1 year of age. Symptoms indicate a primary deficiency in the enzyme dihydroorotate dehydrogenase, the rate-limiting step in de novo pyrimidine synthesis, which could lead to a functional dependence on exogenous uridine.

Treatment. At 3 years of age treatment began with uridine. At 4.5 yrs the treating agent was switched to triacetyluridine because it is a more easily absorbed form of uridine.

Results. CMZ has flourished. Her seizures have decreased from twice a month to once every 2 months. Motor and language development have markedly improved. She is learning her alphabet, knows her colors, and has begun using two word sentences. Mild truncal ataxia persists. A follow-up brain MRI after 20 months on uridine showed no progression in her white matter disease. There has been no biochemical, hematologic, or clinical toxicity, although one additional seizure was noted within 10 days of starting triacetyluridine. The initial triacetyluridine dose was 0.1 g/kg/day. Within 2 months of a dose increase to 0.2 g/kg/day there was a rapid increase in expressive language acquisition and a narrowing of her previous broad-based, ataxic gait. She has recently been increased to 0.3 g/kg/day and has begun 0.75 g of calcium pyruvate TID.

Conclusion. Treatment of MARIAHS syndrome by administration of triacetyluridine results in a dramatic improvement in the patient's condition, and a marked reduction in symptomotology.

Example 3

Treatment by Administration of Triacetyluridine to a Subject Having a Variety of Symptoms and a Familial History of Mitochondrial Disease Patient. KL is an adult who first came to the investigator's attention after the diagnosis of her son with mitochondrial disease leading to stroke-like episodes, ataxia, and encephalopathy. Before administration of triacetyluridine, KL suffered with recurrent pyelonephritis, infection-association neutropenia, hemiplegic/aphasic migraines, grand-mal seizures, neurogenic bowel and bladder requiring QID catheterization, biliary dyssynergia, dysphagia and pc cough, peripheral and autonomic polyneuropathy, painful paresthesias, cardiac conduction disturbances with SVT and tachy-brady syndrome, severe orthostatic hypotension, orthopnea, and poor functional capacity with inability to climb a flight of stairs without stopping to rest, and declining cognitive performance with episodes of clouded sensorium and poor memory that would last hours to days.

Treatment. KL started triacetyluridine at a dose of 0.05 g/kg/d.

Results. Since starting triacetyluridine, KL has not had a seizure or migraine.

Her painful paresthesias are gone, although some numbness persists. She is able to void spontaneously on most days, requiring I&O cath only 1-2 times a week. Pain of biliary dyssynergia is gone. After 6 weeks of triacetyluridine she was able to walk a full mile—a task she has not been able to perform for the past two years because of inadequate functional capacity. Tachy-brady syndrome persists. She wears an exercise, wrist digital pulse meter with alarms set for below 50 and over 140 bpm. The tachy alarms now only on hills and stairs, while previously it would alarm upon simple rise to stand. The brady alarms with rates into the 40s while sleeping 2-3 nights a week. Her sensorium has cleared and she reports her memory "is the best it has been in 5 years." There have been no biochemical or hematologic toxicities.

For the first 10 weeks of triacetyluridine therapy, KL's menstrual cycles shortened from every 4 weeks to every 2 weeks, and her cystic breast disease flared slightly. Intramenstrual estradiol, progesterone, FSH, and LH levels revealed a persistent luteal phase. She did not become anemic. Her Hgb remained stable at 13 g/l. After 10 weeks her menstrual cycle returned to normal, without any change in triacetyluridine or other medication. She is now receiving 0.1 g/kg/day of triacetyluridine and 0.75 calcium pyruvate TID.

Example 4

Treatment by Administration of Triacetyluridine to a Subject Having Multiple Mitochondrial Deletion Syndrome Patient. SF is an 11 year old boy with refractory epilepsy since age 4. As a 5$^{th}$ grader he was able to play little league baseball. Subsequently, he was found to have what appeared to be a multiple mitochondrial DNA deletion syndrome. This disorder produces multiple deleted copies of mitochondrial DNA and can lead to a number of symptoms. SK began deteriorating. He had 2 ICU admissions for crescendo epilepsy, and had 7 changes in his anticonvulsant regimen in the succeeding 4 months. He was having 8-10 grand-mal seizures every night, leaving him postictal for much of the morning. He also developed upper lip automaticity.

Treatment. The patient was initially administered 0.05 g/kg/day of triacetyluridine for one week, followed by 0.16 g/kg/day for 1 week, and then 0.24 g/kg/day.

Results, His seizures and involuntary lip movements stopped completely in the first three days of emergence of his upper lip automaticity. Because his tegretol was found to be subtherapeutic (it was 4 µg/ml both before and after starting triacetyluridine), his tegretal dose was increased, with the aim of achieving therapeutic levels of 8-12 µg/ml, and his triacetyluridine was increased to 0.16 g/kg/day. After three weeks, his dose of triacetyluridine was increased to 0.24 g/kg/d and 0.5 g calcium pyruvate TID was added. This resulted in a transient escalation in his nocturnal seizure activity, which after 3 days, decreased to zero. For several weeks, SF was able to return to school and play little league baseball again.

Example 5

Treatment by Administration of Triacetyluridine to a Subject Having Leigh Syndrome Patient. CS was a 2 year old girl with Leigh syndrome, lactic acidemia, and renal tubular acidosis who suffered a hypertensive crisis and acute edema as she came out of general anesthesia for replacement of an elective percutaneous gastrostomy tube (PEG). The gastrostomy tube was needed only because her daily bicarbonate requirements were so great (25 mEg/kg/day), that she could not meet her needs without a tube in her stomach to introduce the bicarbonate. She developed pneumonia as a complication of PEG and developed new Leigh syndrome lesions in the spinal cord, midbrain, and thalamus. She drifted into a coma 3 days after PEG placement.

Treatment. CS received emergency treatment with triacetyluridine.

Results. The patient's renal tubular acidosis completely resolved within 12 hours of starting triacetyluridine. She did not require any further supplemental bicarbonate, her aminoaciduria improved, and plasma amino acids returned to normal ranges within 2 hours of triacetyluridine, while receiving continuous parenteral nutrition. Despite a favorable biochemical response, she never awoke from her coma, and died after a 4 week terminal illness.

While the invention has been described in detail with reference to certain preferred embodiments thereof, it will be understood that modifications and variations are within the spirit and scope of that which is described and claimed.

What is claimed is:

1. A method for the treatment of a mitochondrial disorder, the method consisting of administering to a subject having such disorder an effective amount of L isomer or D isomer of a keto tautomer or an enol tautomer of a compound, the keto tautomer having the Formula I, and the enol tautomer having the Formula IA:

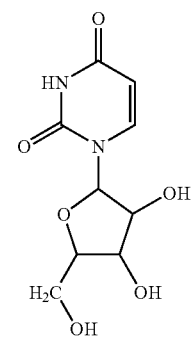

I

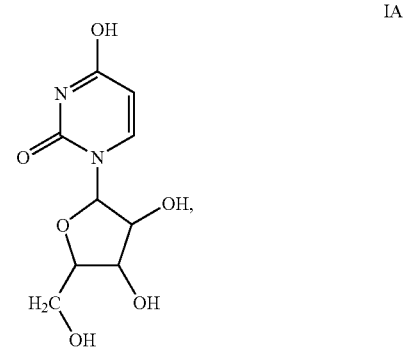

IA wherein the mitochondrial disorder is MARIAHS syndrome.

2. The method according to claim 1, wherein the mitochondrial disorder comprises a deficiency in a pyrimidine synthetic pathway.

3. The method according to claim 2, wherein the deficiency in a pyrimidine synthetic pathway is the deficiency in the uridine synthetic pathway.

4. The method according to claim 2, wherein the deficiency is reduced expression and/or activity of an enzyme in the pyrimidine synthetic pathway.

5. The method according to claim 4, wherein the enzyme is selected from the group consisting of dihydroorotate dehydrogenase (DHOD) and uridine monophosphate synthetase (UMPS).

6. The method according to claim 1, wherein the mitochondrial disorder results in lower than normal uridine levels.

7. The method according to claim 1, wherein the mitochondrial disorder is the result of prior or concurrent administration of an inhibitor of DHOD.

8. The method according to claim 7, wherein the DHOD inhibitor is Leflunomide or Brequinar.

9. The method according to claim 1, further comprising the administration of one or more co-factors, vitamins, or mixtures of two or more thereof.

10. The method according to claim 9, wherein the co-factor is one or both of Coenzyme Q10 or calcium or magnesium pyruvate.

11. The method according to claim 9, wherein the vitamin is selected from the group consisting of thiamine (B1), riboflavin (B2), niacin (B3), pyridoxine (B6), folate, cyanocobalamine (B12), biotin, α-lipoic acid, and pantothenic acid.

12. The method according to claim 1, wherein the compound of Formula (I) or Formula (IA) is administered in a daily dosage in the range of about 0.5 g/m² to 20 g/m².

13. The method according to claim 1, wherein the compound of Formula (I) or Formula (IA) is administered in a daily dosage in the range of about 2 g/m² to 10 g/m².

14. The method according to claim 1, wherein the compound of Formula (I) or Formula (IA) is administered in a daily dosage of about 6.0 g/m².

15. A method for the treatment of a mitochondrial disorder, the method consisting of administering to a subject having such disorder a pharmaceutical composition consisting of:
(a) an effective amount of a compound selected from the group consisting of L isomer or D isomer of a keto tautomer or an enol tautomer of the compound; and
(b) a pharmaceutically acceptable vehicle,
wherein the keto tautomer has the Formula I, and the enol tautomer having the Formula IA:

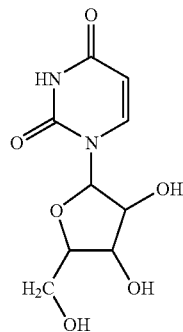

I

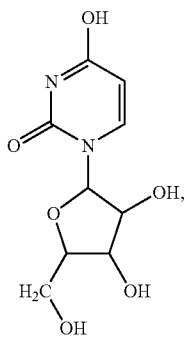

IA wherein the mitochondrial disorder is MARIAHS syndrome.

16. The method according to claim 15, wherein the mitochondrial disorder is associated with a deficiency in a pyrimidine synthetic pathway.

17. The method according to claim 16, wherein the deficiency in a pyrimidine synthetic pathway is the deficiency in the uridine synthetic pathway.

18. The method according to claim 16 wherein the deficiency is reduced expression and/or activity of an enzyme in the pyrimidine synthetic pathway.

19. The method according to claim 18, wherein the enzyme is selected from the group consisting of dihydroorotate dehydrogenase (DHOD) and uridine monophosphate synthetase (UMPS).

20. The method according to claim 15, wherein the mitochondrial disorder results in lower than normal uridine levels.

21. The method according to claim 15, wherein the mitochondrial disorder is the result of prior or concurrent administration of an inhibitor of DHOD.

22. The method according to claim 21, wherein the DHOD inhibitor is Leflunomide or Brequinar.

23. The method according to claim 15, further comprising the administration of one or more co-factors, vitamins, or mixtures of two or more thereof.

24. The method according to claim 23, wherein the co-factor is one or both of Coenzyme Q10 or calcium or magnesium pyruvate.

25. The method according to claim 23, wherein the vitamin is selected from the group consisting of thiamine (B1), riboflavin (B2), niacin (B3), pyridoxine (B6), folate, cyanocobalamine (B12), biotin, α-lipoic acid, and pantothenic acid.

26. The method according to claim 15, wherein the pharmaceutical composition is administered in a quantity providing for delivering the compound of Formula (I) or (IA) in a daily dosage in the range of about 0.5 g/m² to 20 g/m².

27. The method according to claim 15, wherein the pharmaceutical composition is administered in a quantity providing for delivering the compound of Formula (I) or (IA) in a daily dosage in the range of about 2 g/m² to 10 g/ml.

28. The method according to claim 15, wherein the pharmaceutical composition is administered in a quantity providing for delivering the compound of Formula (I) or (IA) in a daily dosage of about 6.0 g/m².

* * * * *